(12) United States Patent
Hepple

(10) Patent No.: US 10,121,460 B1
(45) Date of Patent: Nov. 6, 2018

(54) HUMIDIFIER AND DIGITAL HYGROMETER/THERMOMETER

(71) Applicant: Oasis, Inc., Columbia, MD (US)

(72) Inventor: David Hepple, Columbia, MD (US)

(73) Assignee: Oasis, Inc., Columbia, MD (US)

( * ) Notice: Subject to any disclaimer, the term of this patent is extended or adjusted under 35 U.S.C. 154(b) by 0 days.

(21) Appl. No.: 15/783,216

(22) Filed: Oct. 13, 2017

Related U.S. Application Data

(60) Provisional application No. 62/408,284, filed on Oct. 14, 2016.

(51) Int. Cl.
| | |
|---|---|
| *G10G 7/00* | (2006.01) |
| *G01N 27/22* | (2006.01) |
| *G10D 3/02* | (2006.01) |
| *G01K 13/00* | (2006.01) |
| *B65D 81/26* | (2006.01) |

(52) U.S. Cl.
CPC ........... *G10G 7/005* (2013.01); *G01N 27/223* (2013.01); *G10D 3/02* (2013.01); *B65D 81/264* (2013.01); *G01K 13/002* (2013.01)

(58) Field of Classification Search
CPC ........ G10G 7/005; G01N 27/223; G10D 3/02; G01K 13/002; B65D 81/264
USPC .......................................................... 84/290
See application file for complete search history.

(56) References Cited

U.S. PATENT DOCUMENTS

| | | | | |
|---|---|---|---|---|
| 3,407,700 | A * | 10/1968 | Hollander | G10G 7/00 239/55 |
| 3,721,152 | A * | 3/1973 | Von Meyer | G10D 3/00 239/55 |
| 4,399,404 | A * | 8/1983 | Resh | G01R 1/07 324/666 |
| 4,428,892 | A * | 1/1984 | Berliner | G10G 7/005 239/51.5 |
| 4,572,051 | A * | 2/1986 | Laskin | G10G 7/00 239/57 |
| 4,649,793 | A * | 3/1987 | Blackshear | G10D 3/00 84/453 |
| 5,289,751 | A * | 3/1994 | Light | G10G 7/00 239/51.5 |
| 5,936,178 | A * | 8/1999 | Saari | A24F 25/02 84/453 |
| 6,209,717 | B1 * | 4/2001 | Flynn | G10G 7/005 206/204 |

(Continued)

*Primary Examiner* — Elvin G Enad
*Assistant Examiner* — Christina Schreiber
(74) *Attorney, Agent, or Firm* — Larry J. Guffey, Esq.; Pamela K. Riewerts, Esq.; Oliver & Grimsley, LLC

(57) ABSTRACT

A humidifier and digital hygrometer/thermometer device for use with a stringed, musical instrument having a sound hole includes: (a) a polyvinyl acetate sponge adapted to hold a specified volume of water, (b) a container having an opening adapted to accommodate the sponge and fit within the instrument's sound hole, (c) a case adapted to rest on the instrument's strings , (d) a relative humidity measuring means, (e) a temperature measuring means, (f) a digital display means, (g) a processing element adapted to process the data from the humidity and temperature measuring means and cause the digital display means to display appropriate humidity and temperature measurements, data and further adapted to fit within the case, (h) an adapter affixed to the case and adapted to detachably attach the container to the case.

12 Claims, 4 Drawing Sheets

(56) References Cited

U.S. PATENT DOCUMENTS

| | | | | |
|---|---|---|---|---|
| 6,340,892 B1* | 1/2002 | Rynhart | G01N 27/048 | 324/640 |
| 6,681,661 B2* | 1/2004 | Lalonde | G10D 3/02 | 84/267 |
| 6,959,810 B2* | 11/2005 | Neilson | A45C 11/24 | 206/204 |
| 7,028,914 B1* | 4/2006 | Mair | F24F 6/00 | 236/44 A |
| 8,087,645 B2* | 1/2012 | Hepple | G10G 7/00 | 261/104 |
| 8,220,782 B2* | 7/2012 | Hepple | G10G 7/00 | 239/35 |
| 8,748,723 B1* | 6/2014 | Egberg | G10G 7/00 | 84/453 |
| 9,183,819 B2* | 11/2015 | Hollander | G10D 3/00 | |
| 9,518,949 B1* | 12/2016 | Rognlien | G10G 7/00 | |
| 9,568,203 B1* | 2/2017 | Small | F24F 6/06 | |
| 9,613,604 B1* | 4/2017 | Shearer | G10G 7/00 | |
| 9,880,062 B1* | 1/2018 | Rognlien | G10G 7/00 | |
| 2004/0217026 A1* | 11/2004 | Neilson | A45C 11/24 | 206/314 |
| 2006/0226037 A1* | 10/2006 | Field | A45C 15/00 | 206/314 |
| 2007/0023939 A1* | 2/2007 | Hepple | G10G 7/00 | 261/104 |
| 2009/0174089 A1* | 7/2009 | Hepple | G10D 3/00 | 261/104 |
| 2010/0012739 A1* | 1/2010 | Hoeth | G10G 7/00 | 236/44 C |
| 2010/0170811 A1* | 7/2010 | Coppiardi | A45C 11/00 | 206/14 |
| 2010/0264048 A1* | 10/2010 | Gunsberg | A45C 15/00 | 206/314 |
| 2012/0043394 A1* | 2/2012 | Hepple | G10D 3/00 | 239/34 |
| 2013/0112764 A1* | 5/2013 | Chan | G10D 3/00 | 236/44 C |
| 2013/0193005 A1* | 8/2013 | Hoeth | G10G 7/005 | 206/14 |
| 2014/0123513 A1* | 5/2014 | Ciffin | F26B 9/003 | 34/82 |
| 2016/0042726 A1* | 2/2016 | Glaser | G10G 7/005 | 705/4 |
| 2017/0210524 A1* | 7/2017 | Dougherty | G10G 7/00 | |

\* cited by examiner

HUMIDIFIER AND DIGITAL HYGROMETER/THERMOMETER

CROSS-REFERENCE TO RELATED APPLICATION

This Application claims the benefit of Provisional Patent Application No. PPA 62/408,284, filed Oct. 14, 2016 by the present inventor. The teachings of this application are incorporated herein by reference to the extent that they do not conflict with the teaching herein.

BACKGROUND OF THE INVENTION

1. Field of the Invention

The present invention relates generally to the fields of gas and liquid contact apparatuses and temperature and humidity measuring instruments. More particularly, the present invention relates to a humidifier and digital hygrometer/thermometer device for use with a stringed, musical instrument for which the humidity surrounding and within the instrument needs to be maintained to within a specifiable, instrument-warranty level.

2. Description of the Related Art

Most modern stringed instruments are made of wood. One of the limitations of wood as a material is that it is affected by changes in atmospheric humidity. Increased humidity can cause the wood in the instrument to expand. Decreases in humidity can cause the wood of the instrument to contract.

Research has shown that relative humidity less than 40% can remove water from the wood in the instrument. These changes will affect the tone of the instrument. These changes can also cause the material of the instrument to fail, especially if the wood in the instrument contracts and thereby risks cracking or splitting joints between pieces of wood. In the event that the wood cracks or joints split, the instrument is rendered inoperable.

All musicians are aware of the danger of humidity changes to their instrument and many will use some type of especially-designed-for-use-with-musical-instruments humidifiers to try to control the humidity levels around and within their instruments. Such humidifiers include those disclosed in U.S. Pat. Nos. 3,407,700, 5,289,751, 5,829,452, 5,936,178, 6,244,432, 6,375,000, 8,087,645, and 8,220,782.

But, for these humidifiers to properly perform, they must be maintained; usually by periodically refilling them with water. However, these humidifiers generally do not come with any type of an indicator that warns their users of when maintenance needs to be performed on the humidifier.

Furthermore, to ensure the continuing proper care of such a musical instrument, one would ideally like a documented history of the environment to which the instrument has been exposed rather than just the instrument owner's random inspections of the instrument to assess its condition. For example, professional musicians frequently play in different venues and in traveling between such venues will, under the terms of their travel, have to surrender their instrument to others who will be responsible for its transport (e.g., the luggage handlers for an airline). In these circumstances, the instrument will usually travel for this period of transport in a different environment than the musician.

During this period, it would be helpful if the instrument were to travel with an instrumentation device that was capable of monitoring and periodically recording measurements of various variables (e.g., humidity and temperature) which would document the environment to which the instrument was exposed. Such a record could, for example, indicate whether the humidity and temperature levels surrounding the instrument were maintained to within the instrument's specified, instrument-warranty levels. In the event the instrument were to arrive at its destination in a damaged condition, this type of record could serve as documentation to provide a basis for a possible claim for the damages inflicted to the instrument against the transporter of the instrument.

Unfortunately, there is no single device currently on the market that: (a) acts like a humidifier to provide for the proper humidity levels in the environment surrounding his/her instrument, (b) informs the musician of when maintenance is due on the humidifier that the musician is using with his/her musical instrument, and (c) informs the musician of the environment to which his/her instrument has been exposed during the period when the musician has had to give it up for transport or storage. A need therefore exists for such a device for use with stringed, musical instruments.

DESCRIPTION OF THE PREFERRED EMBODIMENT

Figure 1:
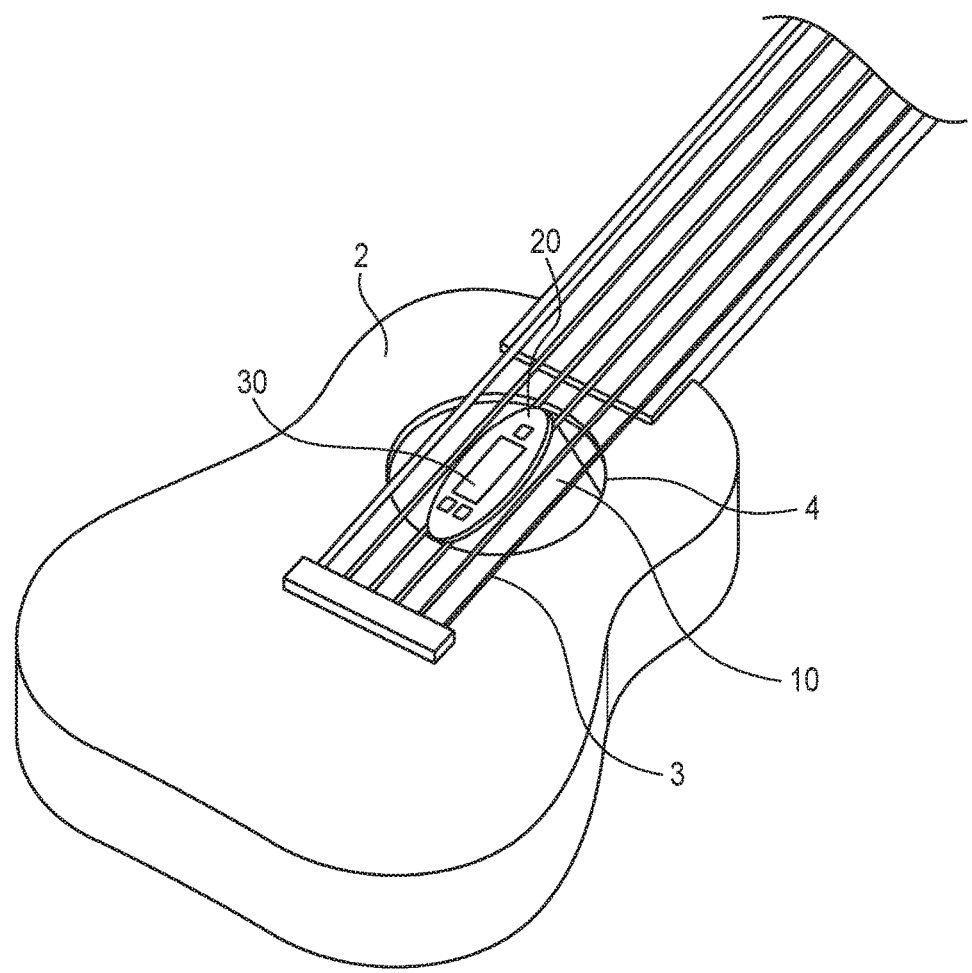
FIG. 1 is schematic representation of the present invention when it is inserted into a guitar.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention generally relates to a humidifier and digital hygrometer/thermometer device for use with a stringed, musical instrument for which the humidity surrounding and within the instrument needs to be maintained to within a specifiable, instrument-warranty level.

The present invention is configured such that it can: (a) acts like a humidifier to provide for the proper humidity levels in the environment surrounding his/her instrument, (b) inform the musician of when maintenance is due on the humidifier that the musician is using with his/her musical instrument, and (c) inform the musician of the environment to which his/her instrument has been exposed during the period when the musician has had to give it up for transport or storage.

The present invention or device includes a display that shows the current relative humidity and temperature in the vicinity of the device. It also has the ability to display the minimum and maximum humidity or temperature experienced in the vicinity of the device during a given time period. The limits of this time period can be set by pushing a reset button on the device. For example, before closing an instrument's case in which the device is to be situated, one pushes the reset button and to eliminate the prior data in the device. Upon the completion of the given time period when the instrument was in the case, the device has the capability to provide a reading of the high and low humidity and temperature experienced during the time period.

FIG. 1 shows a schematic representation of the present invention 1 when it has been inserted into a guitar 2. The present invention's container 10, which is suspended below its case 20, holds a polyvinyl acetate sponge and the container is seen to have been inserted between the strings 3 of the guitar and down through its sound hole 4. Also shown is the digital display 30 which is mounted on the case of the present invention. This display, when situated as shown in FIG. 1, provides continuous readings of the humidity and temperature in and around the guitar's sound hole.

This case 20 is seen to have parallel top 21a and bottom 21b surfaces that both have an elliptical-shaped boundary edge. Extending from this boundary edge is a case sidewall 21c that connects these top and bottom surfaces and encloses the interior volume of the case.

Figure 2:
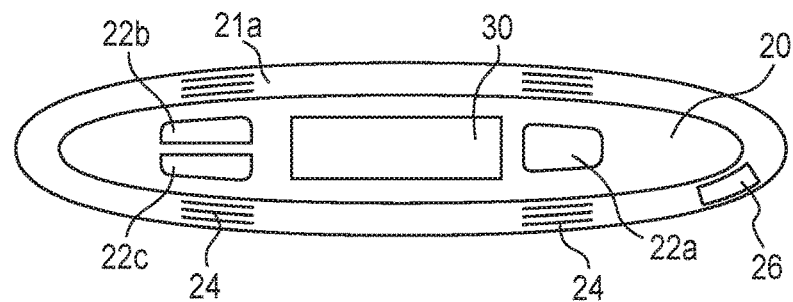
FIG. 2 is a top view of the present invention.

FIG. 2 is a top view of the present invention which shows in more detail its digital display 30 that shows the current humidity and temperature readings in the environment surrounding the case. Also seen on the face of the case 20 are various control buttons that connect with the device's processing element or circuitry which is designed and programmed to control the operation of the device. These include on/off 22a, max/min/clear 22b, and set 22c buttons.

On the case sidewall are slots 24 that are designed to allow for airflow into the case so as to allow the air from the surrounding environment to come into contact with the humidity and temperature sensors of the device. Proximate the slots on the bottom, right hand surface of the case is an access door 26 to the space that holds the battery that provides power to the device.

Figure 5:
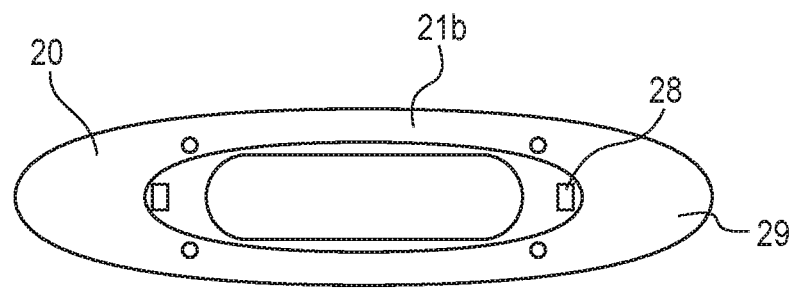
FIG. 5 is an upward view of the underside of the present invention's case.

Shown in FIG. 5 is an upward view of the bottom 21b surface of this case 20. It is seen to have a case adaptor 28 that is designed for the detachable mating of the top of sponge's container 10 with this adaptor so as to temporarily lock the container to the device's case when the device is in service. This container must be detachable in order to provide access to its sponge 50 that periodically needs refilling with water.

This case adapter 28 is adapted to interact with an adapter 12 near the container's open end so as to detachably attach the container to the case's bottom surface so that the container's centerline 14 extends approximately perpendicularly to the case's bottom surface. Additionally, there can be seen on the far left side of the bottom surface of the case a F/C switch 29 that can be used to set whether the temperature data of the device is displayed in either Fahrenheit or Centigrade degrees.

Figure 3:
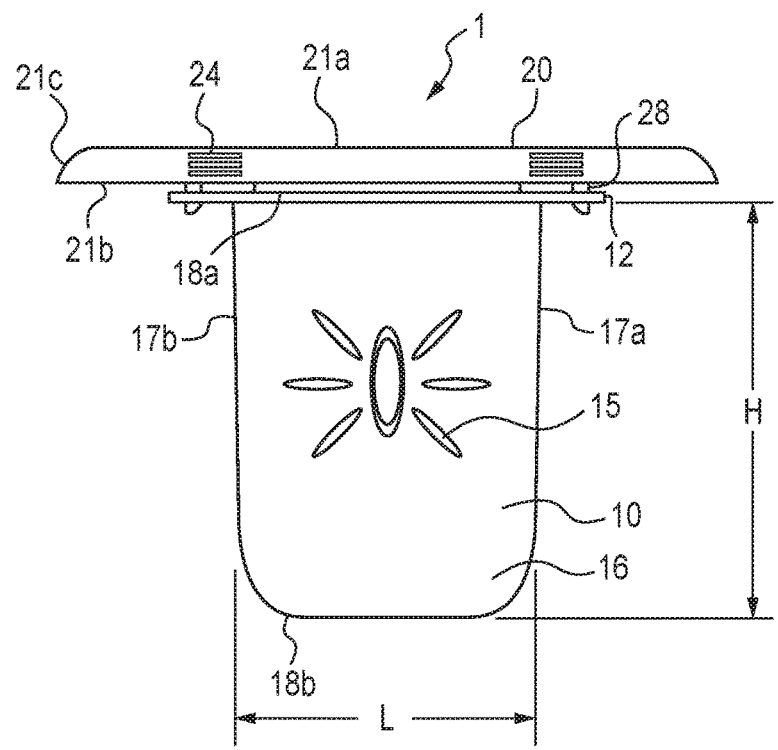
FIG. 3 is a front view of the present invention.

Shown in FIG. 3 is a front view of the present invention. The top of its sponge-storing container 10 is also seen to have a container adaptor 12 that is designed to mate with the case's adaptor 28 for the temporarily locking together of the container and the case 20. Also seen are the holes 15 in the container that allow water to escape the container and humidify the area around the container.

The container 10 is seen to have an enclosing sidewall 16 with opposing parallel sides 16a, 16b that are separated by a distance that defines the width, W, of said container. It has right 17a and left 17b edge portions that connect to the opposing parallel sides and wherein the distance between these edge portions defines the length, L, of the container. It's proximal, open 18a end and distal 18b end are separated by distance, measured along the centerline between these ends, that defines the height, H, of the container.

An opening 19 with a lip is located at the proximal end of the container sidewall and this opening provides entry to the interior space of the container which is adapted to accommodate a polyvinyl acetate sponge. The opposing parallel sidewalls of the container have holes 15 that are airway passages that connect the container's interior space with the environment surrounding the container. Its lip has a connector 12 that extends upwardly from the lip and is used to detachable connect the container to the case.

Figure 6:
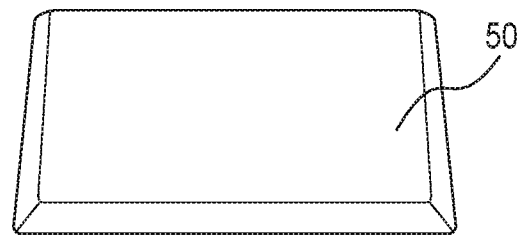
FIG. 6 is a perspective view of the polyvinyl acetate sponge of the present invention.

The polyvinyl acetate sponge 50, shown in FIG. 6, is designed to hold between 25-55 cubic centimeters of water. This is generally sufficient to hydrate a medium-sized guitar instrument for approximately two to three weeks or more assuming that it is stored and used in environments which exhibit standard levels of humidity and temperature.

Figure 4:
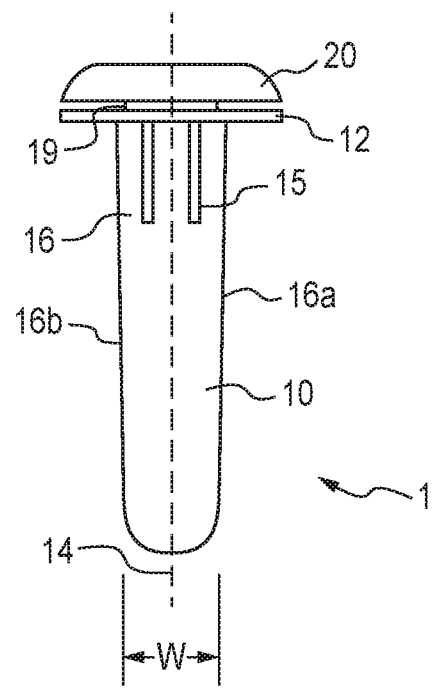
FIG. 4 is a side view of the present invention

FIG. 4 shows a side view of the present invention and how the container detachably connects to the case. FIGS. 1-4 also have representative dimensions given for various elements of the present invention. These dimensions are chosen so that the width, length and height of the container are such that the container, when in use, fits between the parallel, spaced-apart strings of a musical instrument and passes through the instrument's sound hole so that the distal end of the container is situated in the instrument's sound box when the bottom surface of the device's case rests against the top side of the instrument's parallel, spaced-apart strings.

The electronics of the present invention include, in addition to the digital display, various elements that are sized to fit within the device's case and be located proximate to its digital display. These elements include: (a) a humidity sensor or a first means for measuring the relative humidity at any instant in time and at the location proximate the sensor and for providing a first electrical output signal that is proportional to the sensed humidity level, (b) a temperature sensor or a second means for measuring the temperature at any instant in time and at the location proximate the sensor and providing a second electrical output signal that is proportional to the sensed temperature, (c) a processing element adapted to: (i) receive the first electrical output signal and cause the digital display to digitally display the relative humidity measured at any instant time by its sensor, (ii) receive the second electrical output signal and cause the digital display means to digitally display the temperature measured at any instant in time at its sensor's location, and (iii) monitor these output signals so as to capture and store the highest or lowest measured humidity and temperature readings during a period that is marked by the actuation of the set or reset button of the device, (d) appropriate connections to the various buttons that control the operation of the device, and (e) a CR2032 coin cell battery that powers the device.

Since numerous modifications and changes will readily occur to those skilled in the art, it is not desired to limit the invention to the exact construction and operation shown and described herein. Accordingly, all suitable modifications and equivalents may be resorted to, falling within the scope of the invention that will later be set forth in the claims to the invention.

The invention claimed is:

1. A humidifier and digital hygrometer/thermometer device for use with a stringed, musical instrument having a box with a characteristic depth and a sound hole with a characteristic diameter and parallel, spaced-apart strings that pass above said sound hole and wherein said device configured to maintain the humidity within said box to a specifiable level when said musical instrument is not in use and monitor the ranges of temperatures and relative humidity experienced by the device when said device is in use, said device comprising:

a sponge, a container having an interior space and an enclosing sidewall with opposing parallel sides that are separated by a distance that defines the width of said container, and a right and a left edge portion that connect to said opposing parallel sides and wherein the distance between said edge portions defines the length of said container, and proximal and distal ends and a centerline that connects said ends and wherein the distance measured along said centerline between said ends defines the height of said container, and an opening into said container at the proximal end of said container, and wherein the interior space of said container is configured to accommodate said sponge a case having an interior volume and a top surface and a bottom surface, wherein said case is affixed to said container a first means for measuring the relative humidity in the environment surrounding said first means at an instant in time and providing a first electrical output signal, and wherein said first means configured to fit within said case interior volume, a second means for measuring the temperature in the environment surrounding said second means at an instant in time and providing a second electrical output signal, and wherein said second means configured to fit within said case interior volume, a digital display means affixed to said case top surface, a processing element configured to receive said first electrical output signal and cause said digital display means to digitally display said relative humidity measured by said first means, and to receive said second electrical output signal and cause said digital display means to digitally display said temperature measured by said second means, and wherein said processing element configured to fit within said case interior volume, and wherein said width, length and height of said container are chosen so as to enable said container, when in use, to fit between said parallel, spaced-apart instrument strings and to pass through said instrument sound hole so that said distal end of said container is situated in said instrument box when said bottom surface of said case rests against said parallel, spaced-apart instrument strings.

2. The humidifier and digital hygrometer/thermometer device as recited in claim 1, wherein:

said sponge is a polyvinyl acetate sponge configured to hold between 25-55 cubic centimeters of water.

3. The humidifier and digital hygrometer/thermometer device as recited in claim 2, further comprising:

a container adapter proximate said container opening which has a configuration that is configured to detachably connect said container to said case bottom surface.

4. The humidifier and digital hygrometer/thermometer device as recited in claim 3, further comprising:

a case adapter affixed to said case bottom surface and configured to interact with said container adapter so as to detachably attach said container proximal end to said case bottom surface so that said container centerline extends approximately perpendicularly to said case bottom surface.

5. The humidifier and digital hygrometer/thermometer device as recited in claim 4, wherein:

said opposing parallel sides of said container sidewall having holes that connect said interior space of said container with the environment surrounding said container.

6. The humidifier and digital hygrometer/thermometer device as recited in claim 5, wherein:

said processing element further configured to monitor: (a) said first output signal so as to capture and store a first output signal that is chosen from the group of a highest and a lowest measured humidity reading monitored during a period when said device is in use, and (b) said second output signal so as to capture and store a second output signal that is chosen from the group of a highest and a lowest measured temperature reading monitored during a period when said device is in use.

7. The humidifier and digital hygrometer/thermometer device as recited in claim 2, wherein:

said opposing parallel sides of said container sidewall having holes that connect said interior space of said container with the environment surrounding said container.

8. The humidifier and digital hygrometer/thermometer device as recited in claim 1, further comprising:

a container adapter proximate said container opening which has a configuration that is configured to detachably connect said container to said case bottom surface.

9. The humidifier and digital hygrometer/thermometer device as recited in claim 8, further comprising:

a case adapter affixed to said case bottom surface and configured to interact with said container adapter so as to detachably attach said container proximal end to said case bottom surface so that said container centerline extends approximately perpendicularly to said case bottom surface.

10. The humidifier and digital hygrometer/thermometer device as recited in claim 9, wherein:

said opposing parallel sides of said container sidewall having holes that connect said interior space of said container with the environment surrounding said container.

11. The humidifier and digital hygrometer/thermometer device as recited in claim 1, wherein:

said opposing parallel sides of said container sidewall having holes that connect said interior space of said container with the environment surrounding said container.

12. The humidifier and digital hygrometer/thermometer device as recited in claim 1, wherein:

said processing element further configured to monitor: (a) said first output signal so as to capture and store a first output signal that is chosen from the group of a highest and a lowest measured humidity reading monitored during a period when said device is in use, and (b) said second output signal so as to capture and store a second output signal that is chosen from the group of a highest and a lowest measured temperature reading monitored during a period when said device is in use.

\* \* \* \* \*